(12) United States Patent
Bäck et al.

(10) Patent No.: US 6,361,318 B1
(45) Date of Patent: Mar. 26, 2002

(54) METHOD AND ARRANGEMENT FOR PRODUCING ELONGATE SUPPORT ELEMENT AND PRODUCT, AND USE OF THE SUPPORT ELEMENT

(75) Inventors: Tomas Bäck; Lennart Carlsson, both of Mölndal; Anders Petersson, Göteborg, all of (SE)

(73) Assignee: Nobel Biocare AB, Goteborg (SE)

( * ) Notice: Subject to any disclaimer, the term of this patent is extended or adjusted under 35 U.S.C. 154(b) by 0 days.

(21) Appl. No.: 09/423,090
(22) PCT Filed: May 7, 1998
(86) PCT No.: PCT/SE98/00835
§ 371 Date: Jan. 3, 2000
§ 102(e) Date: Jan. 3, 2000
(87) PCT Pub. No.: WO98/51232
PCT Pub. Date: Nov. 19, 1998

(30) Foreign Application Priority Data

May 16, 1997 (SE) .............................. 9701824

(51) Int. Cl.⁷ .............................. A61C 5/00; A61C 8/00
(52) U.S. Cl. .................... 433/215; 433/173; 433/201.1
(58) Field of Search .................. 433/215, 223, 433/173, 174, 201.1

(56) References Cited

U.S. PATENT DOCUMENTS

| | | | |
|---|---|---|---|
| 5,690,843 A | * 11/1997 | Schmitt et al. | 433/223 X |
| 5,816,810 A | 10/1998 | Antonson et al. | |
| 5,851,115 A | 12/1998 | Carlsson et al. | |
| 5,857,853 A | * 1/1999 | Van Nifterick et al. | 433/223 X |
| 5,938,446 A | * 8/1999 | Andersson et al. | 433/223 |
| 5,993,214 A | * 11/1999 | Persson | 433/223 |

* cited by examiner

Primary Examiner—Nicholas D. Lucchesi
(74) Attorney, Agent, or Firm—Connolly Bove Lodge & Hutz, LLP

(57) ABSTRACT

A method and apparatus for producing an elongate support element for a replacement structure in a human body part such as the jaw. The support element is applied to implants in the jaw with great accuracy of fit. Identification information and supplementary information is delivered to computer equipment. Using the information, the computer equipment extracts control data for milling equipment which mills out the support element from a blank. Using the milling information, the milling equipment forms the support element according to a shape determined in the computer equipment. In addition, the information comprises details on the configuration of seats for the implants, and the positioning of the seats in the support element material.

2 Claims, 2 Drawing Sheets

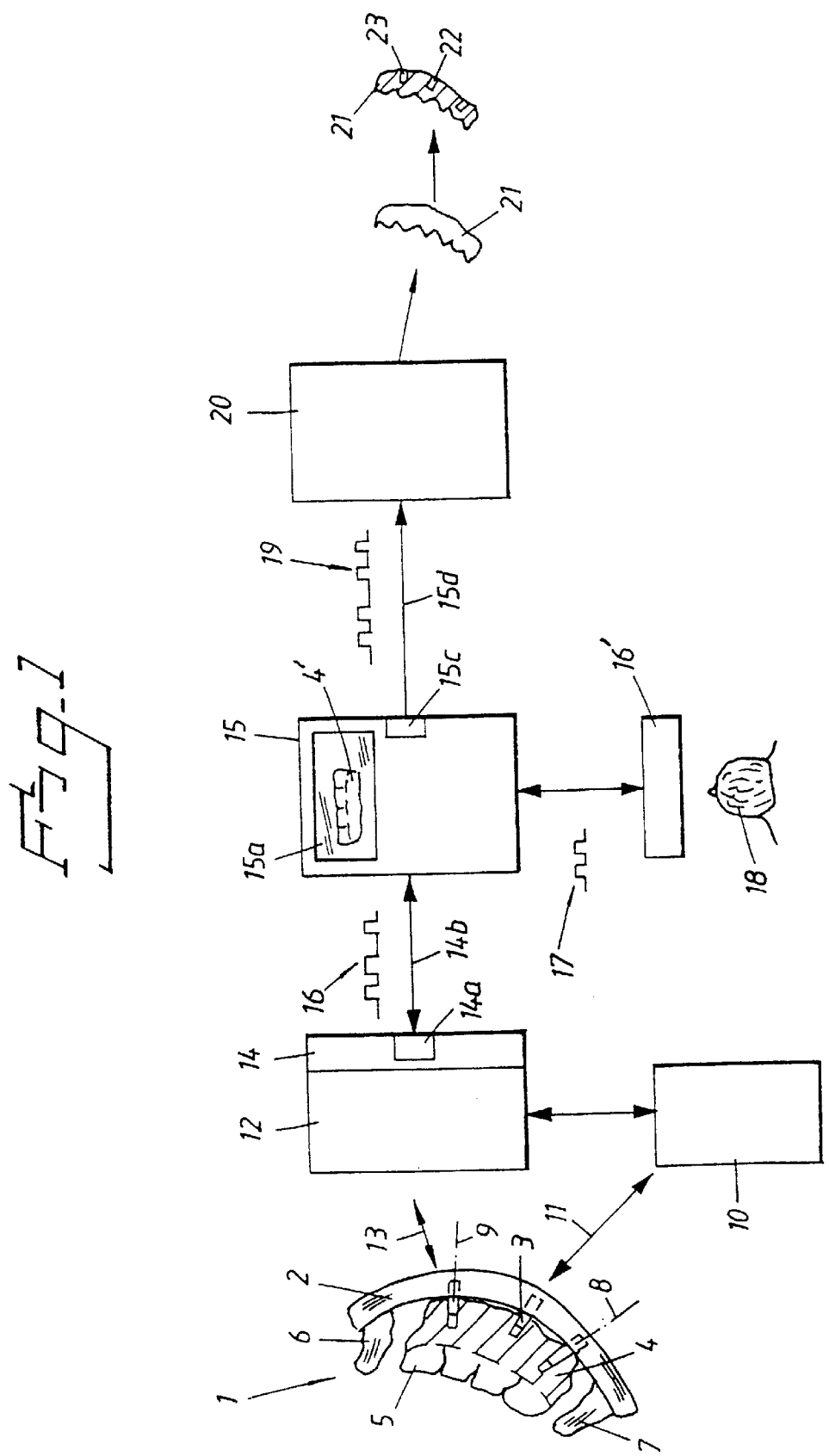

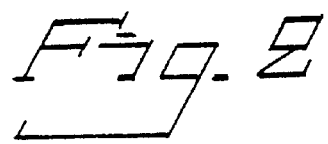
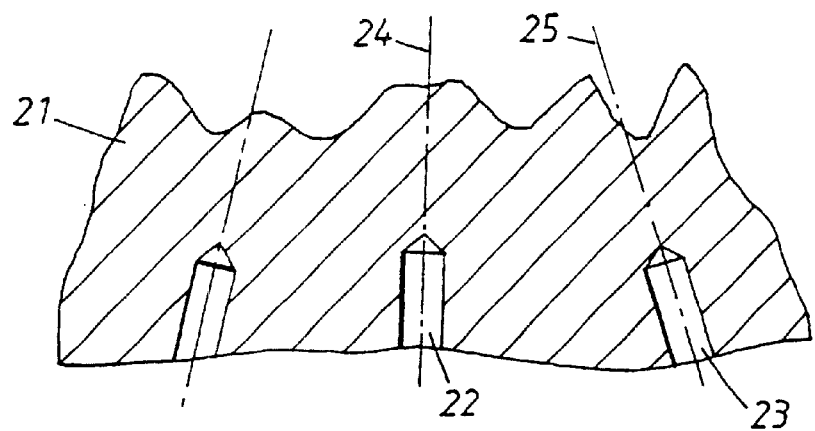
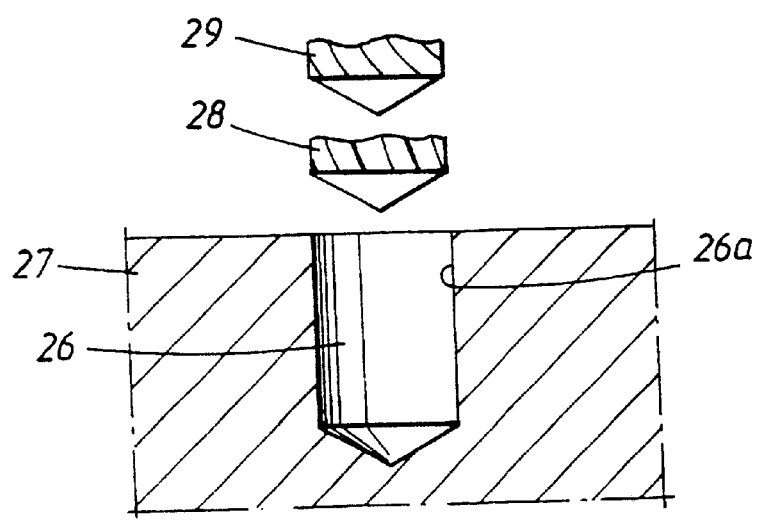

US 6,361,318 B1

METHOD AND ARRANGEMENT FOR PRODUCING ELONGATE SUPPORT ELEMENT AND PRODUCT, AND USE OF THE SUPPORT ELEMENT

TECHNICAL FIELD

The present invention relates inter alia to a method for producing an elongate support element with associated seats for replacement structure in human body parts (jaw). By means seats of the support element can be applied to implants and/or to spacers on these implants. The longitudinal axes or center axes of the seats connect with or are parallel to the longitudinal axes or center axes of the implants in order to satisfy set accuracy of fit requirements which can be about 2/100 mm. The method starts from the stages of identification and possible modelling of the dental situation in question, supplying information, extracted from the identification and modelling, to computer equipment, operating the computer equipment to use the supplied information and further information input to the computer to simulate and determine the structure of the support element in or at the replacement structure. The method further includes; extracting, from the computer equipment, milling coordinates information or milling coordinates data used for controlling the milling of a blank in milling equipment, transmitting the milling coordinates information and milling coordinates data to the milling equipment and controlling the milling work equipment to produce the support element from the blank.

The invention also relates to an arrangement for producing an elongate support element with associated seats for replacement structure in human body parts/jaw, via by means of which seats the support element can be applied to implants and/or to spacers on these implants, where the center axes of the seats are arranged to connect with or be parallel to the center axes of the implants so that set accuracy of fit requirements are satisfied. The arrangement comprises identification members and possibly modelling members for identification and, respectively, modelling of the respective dental situation. Also included is computer equipment for receiving information extracted from the identification and modelling. Also included are first transmission members for transmitting the extracted information to the computer equipment, with which, on the one hand, the structure of the support element and the positioning in or at the replacement structure can be simulated and can be determined by means of the extracted information and further information input to the computer equipment, and; On other hand, milling coordinates information or milling coordinates data for controlling the milling of a blank in milling equipment can be executed with the aid of the said extracted and input information. Also included are second transmission members for transmitting the milling coordinates information (data) to the milling equipment for controlling the latter to produce from the blank.

The invention also relates to a product in the form of an elongate support element for a replacement structure (for example, dental bridge) for the human body, where the support element is designed with seats by means of which the support element can be applied to implants and/or to spacers on these implants. In accordance with the above, the center axes of the seats connect with the center axes of the implants so that fixed accuracy of fit requirements result.

The invention also relates to the use of recessing directly in the material of a blank in conjunction with the production of a dental product from the blank in milling equipment.

STATE OF THE ART

The features discussed in the introduction are known in the production of dental products, and also to some extent in connection with dental products in the form of elongate support elements of the described type. Reference is made to, inter alia, Swedish patents 9304042-6 and 9402351-2. It is also known to make recesses in dental products by means of so-called direct milling of the product material.

DESCRIPTION OF THE INVENTION

Technical Problem

In connection with the abovementioned methods and arrangements for producing dental products in the form of support elements, there are requirements for very great accuracy in the seat application. The required accuracy is, in accordance with the above, at least about 2/100 mm, and the requirements are set in order to be able to satisfy exact fitting in the jaw or equivalent. Poor fitting gives rise to stresses in the dentine or equivalent and causes discomfort and pain and even collapse of the bone in question, at least in the longer term. This has entailed comparatively technically complicated methods and arrangements for seat applications. The said methods include, inter alia, seat production by means of electro-erosion, in which a produced model is used as electrode part. The hitherto proposed methods and arrangements can include production of modules which are welded together (by laser welding) to form the final support element. Before the modules are put together, seat application can take place separately in one or more modules, for example by means of mechanical or optical measurement. However, the result of welding is a nonhomogeneous material in which the strength varies in the support element. Cavities may possibly arise in the material on account of the melt zone not penetrating down deep enough. When grinding or surface-machining the support element to adapt the shape, such cavities can become exposed, which means that the exactness or fit accuracy requirements cannot be satisfied. It has also been proposed to produce support parts by means of casting processes. In casting, there is the problem that the material may buckle upon cooling. The surface fineness in the contact seats can never be better than the grain size of the mould material. Particularly in the case of titanium casting, the molten metal can react chemically with the mould material, which can mean that the outermost material layer, about 1 mm thick, is heavily oxidized or forms an alloy, cf., for example in titanium casting, in the form of zirconium oxide in which the surface layer will consist of an alloy of titanium and zirconium. The strength will vary in the support element and there may be problems in obtaining support part elements with acceptable strength. In both welding and casting, the chemical composition of the surface therefore varies. In welding, the weld seam differs from the base material, and, in casting, ground areas differ from the raw cast surface. When ceramic is then to be baked onto the surface to form the tooth replacement, the adhesion varies greatly across the surface, the result of this being that there may be difficulties in obtaining products which are durable in the long term and which are suitable for implanting in, for example, the jaw. There is therefore a need for methods and arrangements and finished support elements, and the use of known methods known, which solve the abovementioned problems. The main object of the present invention is to provide a solution to these problems.

Solution

That which can principally be regarded as characterizing a method according to the invention is that the milling equipment, with the aid of the milling information or milling data, in addition to executing the support element shape determined in the computer equipment from the blank, can also be used for control in order to mill out the said seats directly in or out of the blank/support element material.

The arrangement according to the invention can principally be regarded as being characterized in that the milling coordinates information or milling coordinates data is designed, in addition to executing the support element shape determined in the computer equipment from the blank using the milling equipment, also to be used to control the milling equipment to shape and position the seats directly in the blank/support element material using the information likewise set in the computer equipment.

A product according to the invention can principally be regarded as being characterized in that the support element is made of homogeneous material and in that each seat wall is executed directly from the homogeneous support element material.

In embodiments of the inventive concept for the product, each seat wall can consist of a surface ground directly in the homogeneous material. The product can also have a material strength around each seat which essentially corresponds to the material strength of the rest of the support element material. In a further illustrative embodiment, each seat wall is formed directly from the support element material without intermediate layers of material compositions or material alterations. Each seat wall thus has the same chemical composition as the rest of the support element material.

A use according to the invention can be characterized in that the recessing is used for receiving the seats in the product in the form of a support element included in tooth replacement structure. The said seats must in this case have fixed accuracy of fit requirements in order to be applied to implants located in the human body and/or to spacers on these implants.

In one embodiment for- recessing which is used for forming a seat in the support element with milling equipment, this milling coordinates information is supplied in the form of milling coordinates data executed in database equipment and attributable to identification data on the design of the tooth replacement structure and supplementary data fed to the computer equipment. The information supplied from the computer equipment to the milling equipment can be integrated on condition that it contains milling data on the support part design and the seat design/the seat positions.

Advantages

By means of the measures proposed above, support elements with very accurate seat positions can be produced at a relatively low cost. The advantages are considerable compared to casting, for example. In this case, a material independence is achieved, which means that the production can be carried out using titanium, gold or other tissue-compatible material. The seats are integrated in the material and better precision is obtained in the seat positions in relation to the cast support elements. The invention also affords advantages compared to partially welded bridges. In this case too, a clear material independence is achieved, and it is possible to avoid weld seams which impair the strength and require more comprehensive re-grinding. In the present case, very good and uniform strength can be obtained throughout the whole material, and the need for re-grinding is reduced.

DESCRIPTION OF THE FIGURES

A presently proposed embodiment of the method, the arrangement, the support element and the use will be described hereinbelow with reference to the attached drawing, in which:

FIG. 1 shows a block diagram of the structural parts of the arrangement, and the various manufacturing stages in the method, FIG. 2 shows, in vertical cross-section, an example of a support element, and FIG. 3 shows in vertical cross-section, and in an enlarged view compared to FIG. 2, a seat formation in a support element.

DETAILED EMBODIMENT

In FIG. 1, reference number 1 indicates a dental situation in the form of a mandible 2. The dental situation is such that a replacement part in the form of a dental bridge is to be applied to implants 3 incorporated in the jaw. The designs of the implants with spacers and the like are already well known and will not be described here. In the dental situation, the dental bridge has been illustrated in its final state so as to indicate, in this application, a tooth replacement example which is appropriate to the invention. The replacement structure or the dental bridge will, in the final state, comprise a support part 4 and, applied to this, a tooth replacement material which is symbolized by 5. The tooth replacement structure is placed between existing teeth 6 and 7 on the patient. The implants have individual inclinations on their center axes, and the center axes for two of the implants are indicated by 8 and 9. The dental situation 1 in question which is to be read off on commencement of the work thus includes the human jaw 2, the implants 3 and possibly also surrounding teeth 6 and 7. In connection with the production of the support element 4, modelling equipment can be used which is symbolized by 10 in the figure. The cooperation between the situation and the equipment 10 is symbolized by arrows 11.

In accordance with the invention, the dental situation is to be read off using identification equipment 12 which can also be of a known type. The reading can be effected in various known ways, for example by stereophotography, scanning of the outer form, etc. The scanning of the outer form can be performed using scanning needles, optical light beams, etc. The identification function is symbolized by 13 in the figure. The identification in question leads to a conversion to electrical information signals. This conversion takes place, in the illustrative embodiment, in conversion equipment 14. The conversion equipment also comprises first transmission members 14a by means of which information on the identified situation can be transmitted to computer equipment 15 of a known type in the known context known. According to the illustrative embodiment, the transmission is done digitally and identification data is indicated by 16. This identification data is thus received in computer equipment 15 in a known manner. The computer equipment 15 also includes a terminal 16' by means of which supplementary information is input to the computer equipment. In the illustrative embodiment, the supplementary information is digital and has been symbolized by 17 in FIG. 1. The computer equipment comprises memory equipment and CPU which can receive and store, and, respectively, execute the received information 16 and 17. With the aid of the last-mentioned information or data 16 and 17, the support element 8 can be simulated on the computer screen 15a, for example. This applies also to the tooth replacement structure 9 as such. By interaction with a user 18, the simulated support part 4' can be shaped in a known manner for optimum construction in the tooth replacement part 9. Programs for identifying shape, positions, etc., are available on the market and can be used in connection with the illustrative embodiment.

With the aid of the said information 16 and 17 and the simulation which has been performed, milling coordinates information can thus be executed in the computer equipment 15. Examples of milling coordinates data are shown by 19 in the figure. The said milling coordinates data are fed to machining equipment 20 of a known type. The machining equipment consists of a mill which can mill from a blank 21 not only the outer shape 21 of the support part, but also the seats 22, 23 by means of which the support part 21 is to be anchored on the implants 3 and/or on spacers (not shown) on these implants. The inclinations and the positions of the seats are produced using the known programs in the computer equipment and are thus part of the milling coordinates data 19.

In FIG. 2, the positions and inclinations of the seats are shown enlarged in relation to FIG. 1. In FIG. 2, two of the seats have been given reference labels 22 and 23 (cf. FIG. 1). The center axes of the seats are indicated by 24 and 25, respectively. These center axes must be adapted with great precision to the corresponding axes of inclination of the implant (cf. the center axes 8 and 9 in FIG. 1)

FIG. 3 shows that known equipment can be used for making a seat 26 in the support part material 27. In FIG. 3, a mill is indicated by 28. In addition, a grinding member is indicated by 29. The mill can thus mill out the recess 26, after which the seat wall 26a can be re-ground using the member 29. The known equipment 28 for making a hole can thus be used for making the seat 26 in the case according to FIG. 1. The milling equipment 20 can work in a known manner. In FIG. 1, second transmission members are shown by 15c for transmitting the information 19 to the machining equipment 20. This transmission can be done in a known manner and is symbolized by 15d. Thus, for example, the transmission can be done by the telephone and/or computer network, for example via the international computer network, the internet. The transmission between the first transmission members 14, 14a and the computer equipment can take place on a fixed connection, for example when the equipment is integrated or set up in the same locality. However, the transmission, which has been symbolized by 14b in FIG. 1, can also take place via the telephone and/or computer network, for example via the said international network, the internet. Alternatively, one or both transmissions can take place with the aid of cassettes which are sent between the localities in question.

The invention is not limited to the embodiment shown above by way of example, but can be modified within the scope of the appended patent claims and the inventive concept.

What is claimed is:

1. Method for producing an elongate support element with associated seats for a replacement structure in a human body part, said seats enabling the support element to be applied to implants or to spacers on said implants, wherein longitudinal axes of the seats connect with or are parallel to longitudinal axes of the implants in order to satisfy set accuracy of fit requirements, the method comprising the steps of:

a) at least one of identifying and modeling a dental situation;

b) supplying information extracted from step a) to computer equipment;

c) operating the computer equipment to use the supplied information to simulate and determine a structure of the support element in or at the replacement structure;

d) extracting, from the computer equipment, milling coordinates information for controlling the milling of a blank in milling equipment;

e) transmitting the milling coordinates information to the milling equipment, and f) controlling the milling equipment using said milling coordinates information to produce the support element from the blank; wherein:

g) the milling equipment, using said milling coordinates information, in addition to milling the support element shape determined in the computer equipment from the blank, is controlled to mill out said seats directly from the blank/support element material.

2. Apparatus for producing an elongate support element with associated seats for a replacement structure in a human body part, said seats enabling the support element to be applied to implants or to spacers on said implants, wherein center axes of the seats are arranged to connect with or be parallel to center axes of the implants so that set accuracy of fit requirements are satisfied, the apparatus comprising:

at least one of identification means and modeling means for identification and, respectively, modeling of a dental situation;

computer equipment for receiving information extracted from the identification and modeling means; and first transmission means for transmitting the extracted information to the computer equipment, wherein:

a structure of the support element and a positioning of said support element in or at the replacement structure is simulatable and determinable by means of the extracted information input to the computer equipment;

milling coordinates information controls the milling of a blank in milling equipment using said extracted and input information; and second transmission means are arranged for transmitting the milling coordinates information to the milling equipment for controlling said milling equipment to produce the support element from a blank;

and wherein the milling coordinates information, in addition to enabling the milling of the support element shape determined in the computer equipment from the blank using the milling equipment, also controls the milling equipment to shape and position said seats directly in the blank/support element material.

* * * * *